United States Patent [19]

Dettbarn et al.

[11] Patent Number: 4,722,729
[45] Date of Patent: Feb. 2, 1988

[54] NEEDLELESS INJECTION INSTRUMENT

[75] Inventors: Hans-Jürgen Dettbarn, Marburg; Josef Zimmermann, Sulzbach, both of Fed. Rep. of Germany

[73] Assignee: Hoechst Aktiengesellschaft, Sulzbach, Fed. Rep. of Germany

[21] Appl. No.: 35,250

[22] Filed: Apr. 7, 1987

Related U.S. Application Data

[63] Continuation of Ser. No. 757,727, Jul. 22, 1985, abandoned.

[30] Foreign Application Priority Data

Jul. 24, 1984 [DE] Fed. Rep. of Germany ....... 3427187

[51] Int. Cl.4 ............................................. A61M 5/30
[52] U.S. Cl. ......................................... 604/71; 604/68
[58] Field of Search ..................... 604/71, 68, 70, 72; 222/36, 38

[56] References Cited

U.S. PATENT DOCUMENTS

| 1,956,876 | 5/1934 | Chapman | 222/36 |
| 3,080,097 | 3/1963 | Schmaus | 222/38 |
| 3,526,225 | 9/1970 | Hayamamachi | 604/71 |
| 4,188,984 | 2/1980 | Lyall | 222/38 |
| 4,396,384 | 8/1983 | Dettbarn et al. | 604/68 |
| 4,400,171 | 8/1983 | Dettbarn et al. | 604/68 |
| 4,560,377 | 12/1985 | Geat et al. | 604/71 |

FOREIGN PATENT DOCUMENTS 0169494 1/1986 European Pat. Off. ............. 604/71

Primary Examiner—C. Fred Rosenbaum
Assistant Examiner—Gene B. Kartchner
Attorney, Agent, or Firm—Finnegan, Henderson, Farabow, Garrett & Dunner

[57] ABSTRACT

In this needleless injection instrument, the piston pump (17) for the medium to be injected is connected to a drive motor (18). On the motor housing (1) of the drive motor, an operating element (2) is fitted displaceably and a stroke counter (7) for counting the applications is arranged. To the free shaft end (11) of the stroke counter, a control cam (6) is fixed which engages with a control pin (4) supported on a control roll (3) which is located in the operating element (2) for the drive motor (18).

2 Claims, 4 Drawing Figures

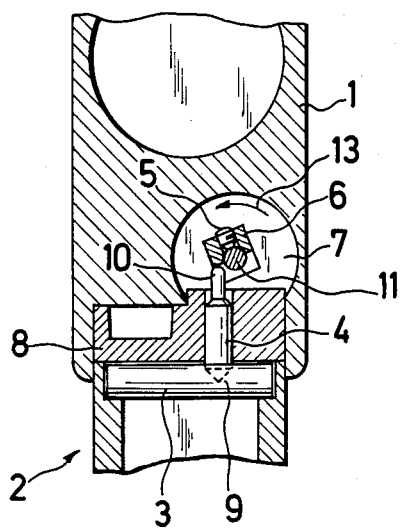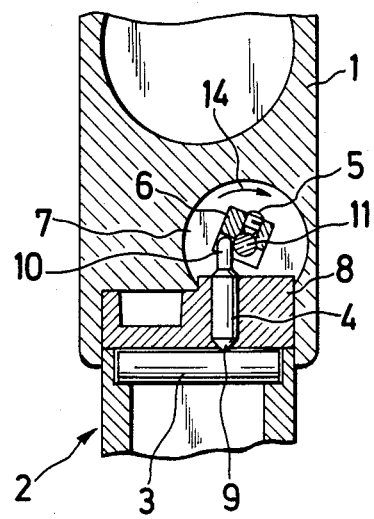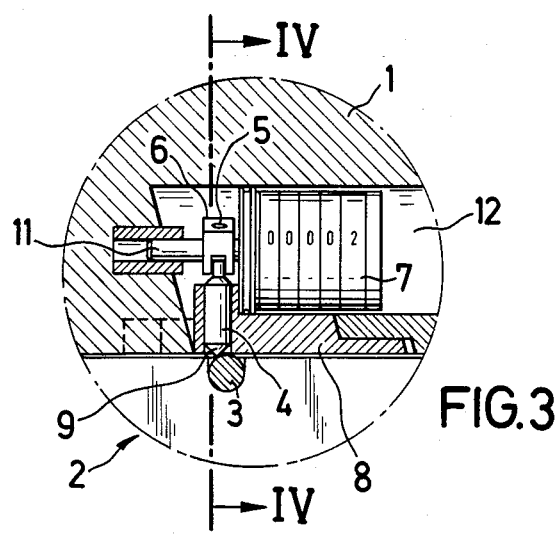

NEEDLELESS INJECTION INSTRUMENT

This application is a continuation of application Ser. No. 757,727, filed July 22, 1985, now abandoned.

BACKGROUND OF THE INVENTION

The invention relates to a needleless injection instrument with a piston pump for injecting medium. The pump is connected to a drive motor. An operating element is displaceably fitted on the motor housing of the drive motor.

Injection instruments of the above type have been disclosed in U.S. Pat. Nos. 4,400,172 and 4,400,171.

It is an object of the present invention to provide these known injection instruments with a mechanism for counting the number of injections. The object is achieved by an injection instrument which comprises a stroke counter which is arranged in the motor housing and to the free shaft end of which a control cam is fixed which engages with a control pin supported on a control roll which is located in the operating element for the drive motor.

BRIEF DESCRIPTION OF THE DRAWINGS

The invention is explained below in more detail be reference to drawings which show only one possible embodiment and in which:

FIG. 2 shows the section II—II of FIG. 1;

FIG. 3 shows a detail "Z" of FIG. 1, wherein the control pin has been lifted off by the control roll, i.e. wherein the injection instrument is discharged; and FIG. 4 shows the section IV—IV of FIG. 3.

DESCRIPTIONS OF THE PREFERRED EMBODIMENT

Figure 1:
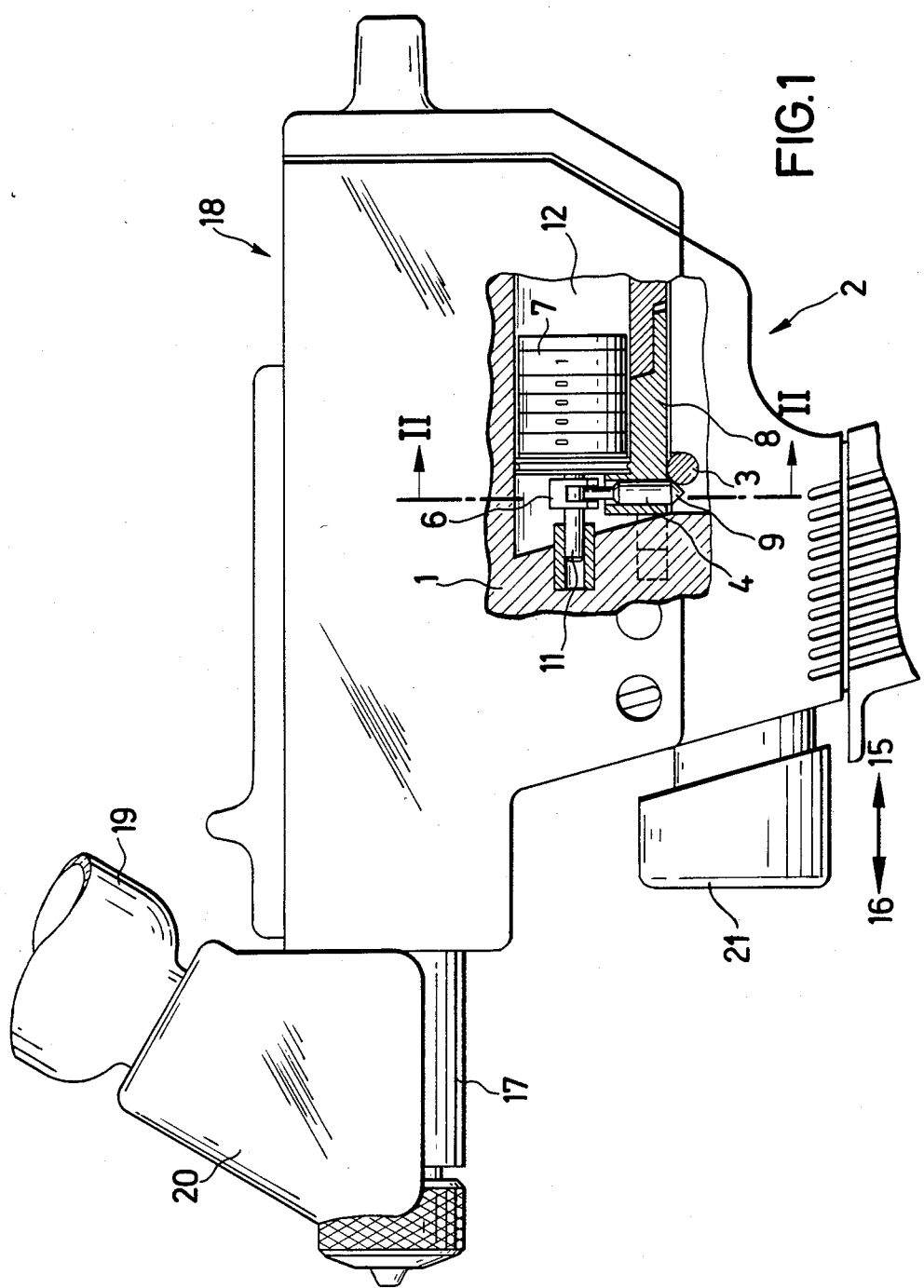
FIG. 1 shows a side view of the injection instrument in the charged state; partically in section.

The needleless injection instrument essentially comprises a vaccine pump 17 for injecting medium. The pump is connected to a drive motor 18. The vaccine pump 17 carries a fitting 20 for vaccine container 19. The operating element 2 for the drive motor 18 is movably fitted to the motor housing 1. In a recess 12 in the motor housing 1, a commercially available stroke counter 7 is fitted. The shaft of counter 7 is provided by the manufacturer with a return spring (not shown). The free shaft end 11 is provided with a control cam 6 which is held on the shaft by a screw 5, as shown in FIG. 2. The control cam 6 engages with the peg end 10 of control pin 4 which is guided in a mounting plate 8 located in the motor housing 1. The conically shaped end 9 of the control pin 4 is supported on a control roller 3 which is located in the operating element 2 for the drive motor 18.

A return spring installed in the stroke counter turns the shaft 11 in the direction of the arrow 13. When the injection instrument is tensioned, by pressing knob 21 once in the direction of arrow 15, the operating element also moves in the direction of the arrow 15. As a result, the control pin moves under the action of the return spring of the stroke counter 7 in the direction of the control roller 3. The shaft 11 of the stroke counter 7 executes a pivoting movement in the direction of the arrow 12 (FIG. 2). When triggering the injection (releasing the injection instrument), by pressing knob 21 a second time in the direction of arrow 15, the operating element 2 is pushed in the direction of the arrow 16. At the same time, the control roller 3 lifts the control pin 4. The peg end 10 exerts pressure on the control cam 6 which is fixed to the shaft end 11 and thus rotates shaft 11 in the direction of the arrow 14. The stroke counter 7 indicator further by one count.

We claim:

1. A needleless injection instrument, for injecting a medicament into a body, comprising:
    a piston pump for injecting said medicament when activated;
    a tensionable and releasable drive motor for activating said pump when released;
    an operating element operatively connected to said drive motor and arranged to move from a first position when said drive motor is tensioned to a second position when said drive motor is released;
    knob means for tensioning said drive motor when pressed once and for releasing said drive motor when pressed a second time;
    a stroke counter for counting the number of injections;
    a cam arranged to actuate the stroke counter when engaged;
    a control pin having a first end for at times engaging said cam, and a second, supportable end, wherein said first end engages said cam when said second end is supported; and
    a roller, operatively connected to said operating element, for supporting said second end of the control pin when said operating element is in said second position.

2. The needleless injection instrument as in claim 1 wherein said control pin second end is conically shaped.

* * * * *